US012721290B2

(12) United States Patent
Yen et al.

(10) Patent No.: US 12,721,290 B2
(45) Date of Patent: Sep. 1, 2026

(54) LEAF VEIN ABSORPTION METHOD AND FUNCTIONAL MODIFICATION MATERIAL FOR PLANT

(71) Applicant: NATIONAL CHENG KUNG UNIVERSITY, Tainan City (TW)

(72) Inventors: Chen-Piao Yen, Tainan City (TW); Sheng-Lung Tu, Tainan City (TW); Jyh-Ming Ting, Tainan City (TW); Yen-Hsun Su, Tainan City (TW)

(73) Assignee: NATIONAL CHENG KUNG UNIVERSITY, Tainan City (TW)

( * ) Notice: Subject to any disclaimer, the term of this patent is extended or adjusted under 35 U.S.C. 154(b) by 336 days.

(21) Appl. No.: 18/534,697

(22) Filed: Dec. 10, 2023

(65) Prior Publication Data

US 2024/0276934 A1 Aug. 22, 2024

(30) Foreign Application Priority Data

Feb. 17, 2023 (TW) ................................ 112105714
Nov. 14, 2023 (TW) ................................ 112143928

(51) Int. Cl.

*A01H 1/00* (2006.01)
*A01H 1/02* (2006.01)
*A01N 43/16* (2006.01)
*A01N 59/06* (2006.01)

(52) U.S. Cl.

CPC ............... *A01H 1/12* (2021.01); *A01H 1/026* (2021.01); *A01N 43/16* (2013.01); *A01N 59/06* (2013.01)

(58) Field of Classification Search

CPC .......... A01H 1/12; A01H 1/026; A01N 43/16; A01N 59/06

See application file for complete search history.

(56) References Cited

FOREIGN PATENT DOCUMENTS

| | | | |
|---|---|---|---|
| CN | 115087739 A | | 9/2022 |
| TW | M621627 U | * | 12/2021 |

OTHER PUBLICATIONS

TW M621627 U machine translation (Year: 2021).*

* cited by examiner

*Primary Examiner* — Sue X Liu
*Assistant Examiner* — Nathan W Schlientz

(57) ABSTRACT

Disclosed are a leaf vein absorption method and a functional modification material for plant. The functional modification material has a covering with a functional material and a protector with a polymeric stabilizing material. The functional material is a unitary, a multivariate, or a high-entropy compound, or a semiconducting or an optoelectronic material. The covering covers a surface of a plant organ, wherein the covering comprises a stomata expansion material to enable the functional material to be absorbed into a plant through stomata. The protector covers a surface of the covering. The functional material is capable of maintaining its functional presence on a surface of the plant until the plant organ undergoes natural apoptosis. Through an absorption technology of leaf veins on the surface of the plant, special functions can be achieved without modifying or implanting plant genes.

6 Claims, 3 Drawing Sheets

LEAF VEIN ABSORPTION METHOD AND FUNCTIONAL MODIFICATION MATERIAL FOR PLANT

CROSS-REFERENCE TO RELATED APPLICATION

This application claims priority from Taiwan Patent Application No. 112105714, filed on Feb. 17, 2023; and claims priority from Taiwan Patent Application No. 112143928, filed on Nov. 14, 2023, each of which is hereby incorporated herein by reference in its entireties.

BACKGROUND OF THE DISCLOSURE

1. Field of Disclosure

The disclosure relates to a plant surface modifier and a plant absorption method, and more particularly to a leaf vein absorption method and a functional modification material for plant.

2. Related Art

Efficient agricultural production has a great potential in the application of global agricultural and horticultural science and technology. However, the combination of plant surface modification technology in the horticulture and biotechnology industries is still in its initial stage. Therefore, there are techniques for modifying the surface of plants by applying functional materials on plants in order to produce special functional properties for horticultural or agricultural applications. However, the current plant surface modification technologies mostly cover the plant surface, leading to loss of plant surface functions and even death. Functional materials cannot stay on the plant surface for a long time. Although modifying or implanting plant genes biologically can achieve special functions, problems such as genetic contamination are prone to occur and it is subject to many restrictions.

SUMMARY OF THE DISCLOSURE

In view of the above, one object of the disclosure is to provide a leaf vein absorption method and a functional modification material for plant to solve the above-mentioned problems of conventional techniques.

This disclosure designs a brand-new leaf vein absorption technology, the leaf vein absorption technology is capable of absorbing unitary, multivariate, or high-entropy compounds, semiconducting or optoelectronic materials to effectively produce special physical or chemical functions. After modification, plants can still grow naturally, the leaf vein absorption technology can be widely applied to natural plants and is capable of effectively advancing progress in horticultural and agricultural functional plants. At the same time, the nighttime carbon dioxide solidification function produced is in line with the international net-zero carbon emission policy to achieve carbon neutrality.

In order to achieve the aforementioned object, the disclosure provides a functional modification material for plant at least comprising a covering with a functional material and a protector with a polymeric stabilizing material, and the covering covers a surface of a plant organ of a plant, wherein the covering further comprises a stomata expansion material, such as fusicoccin, to enable the functional material to be absorbed into the plant through stomata of the plant organ.

The leaf vein absorption method of the disclosure at least comprises: providing a covering with a functional material, the covering being used to cover a surface of a plant organ of a plant, wherein the covering comprises a stomata expansion material for promoting expansion of a plurality of stomata on the surface of the plant organ to enable the functional material to be absorbed into the plant through the stomata of the plant organ, and the covering is a water-based material with an adjustable surface charge that has an adhesiveness of a biogel or a biodegradable gel; and providing a protector with a polymeric stabilizing material, the protector being used to cover a surface of the covering, wherein the protector is another water-based material with the biogel or the biodegradable gel, the polymeric stabilizing material is used to stabilize and polymerize the biogel or the biodegradable gel of the protector and/or the covering, thereby increasing a quantity and a density of the functional material absorbed by the plant organ.

Preferably, the covering is covered on the plant organ by spraying, smearing, or coating, and the protector is covered on the covering by spraying, smearing, or coating.

Preferably, the stomata expansion material is fusicoccin, and the fusicoccin is capable of promoting expansion of the stomata on the surface of the plant organ.

Preferably, a content of the stomata expansion material in the covering is less than or equal to 170 μM.

Preferably, a particle size of the functional material is 2 μm to 5 nm.

Preferably, the functional material is a nanoscale material, a sub-nanoscale material or a micro-nanoscale material.

Preferably, a zeta potential formed by a surface charge of the functional material is +0 to +75 meV.

Preferably, the polymeric stabilizing material of the protector is alum ions that stabilize the biogel or the biodegradable gel by polymerization.

Preferably, a weight percentage of the polymeric stabilizing material in the protector is less than or equal to 35%.

Preferably, the biogel is a soft deer gel, a hard deer gel, an isinglass, a cow gel, a rabbit gel, a granular gel, and/or a sanzenbon glue, and the biodegradable gel is polyamide, polyvinylpyrrolidone and/or polyvinyl acetate.

Preferably, the water-based material of the covering is an acidic water-based substance, wherein the acidic water-based substance is a water-based solvent containing citric acid, succinic acid, tannic acid, salicylic acid, malic acid, ascorbic acid, gallic acid, hydrochloric acid, nitric acid and/or acetic acid.

Preferably, the water-based material of the covering is an alkaline water-based substance, wherein the alkaline water-based substance is a water-based solvent containing sodium bicarbonate, sodium carbonate, sodium hydroxide, potassium bicarbonate, potassium carbonate and/or potassium hydroxide.

Preferably, the functional material is needle-shaped or sea urchin-shaped gold nanoparticles.

In order to achieve the aforementioned object, the disclosure further provides a leaf vein absorption method at least comprising: preparing a covering with a functional material and preparing a protector with a polymeric stabilizing material, wherein the covering covers a surface of a plant organ of a plant, wherein the covering further comprises a stomata expansion material, such as fusicoccin, to enable the functional material to be absorbed into the plant organ through stomata of the plant organ, wherein the plant organ is a leaf or a modified leaf.

A leaf vein absorption method of the disclosure at least comprises: mixing a functional material suspension solvent containing a functional material into a water-based solvent using a biogel or a biodegradable gel, thereby forming an adhesive functional material suspension solvent; mixing the adhesive functional material suspension solvent into an acidic or alkaline water-based solvent, thereby forming an adhesive functional material suspension with an adjustable surface charge to serve as a covering with a functional material; covering a surface of a plant organ of a plant with the covering, wherein the functional material suspension solvent containing the functional material further comprises a stomata expansion material for promoting expansion of a plurality of stomata on the surface of the plant organ, wherein the plant organ is a leaf or a modified leaf; mixing a polymeric stabilizing material into another water-based solvent using a biogel or a biodegradable gel, thereby forming a protector; and covering a surface of the covering with the protector, wherein the polymeric stabilizing material is used to stabilize and polymerize the biogel or the biodegradable gel of the protector and/or the covering, thereby increasing a quantity and a density of the functional material absorbed by the plant organ.

Preferably, the biogel of the protector and/or the covering is a soft deer gel, a hard deer gel, an isinglass, a cow gel, a rabbit gel, a granular gel, and/or a sanzenbon glue, and the biodegradable gel is polyamide, polyvinylpyrrolidone and/or polyvinyl acetate.

Preferably, the stomata expansion material is fusicoccin, and the polymeric stabilizing material is alum ions.

Preferably, the covering is covered on the plant organ by spraying, smearing, or coating, and the protector is covered on the covering by spraying, smearing, or coating.

Preferably, a particle size of the functional material is 2 μm to 5 nm.

Preferably, a zeta potential formed by a surface charge of the functional material is +0 meV to +75 meV.

Based on the above, the leaf vein absorption method and the functional modification material for plant of the disclosure have the following advantages:

(1) By using nano leaf vein absorption technology, plant functions are not damaged and can coexist.

(2) The functional material is capable of maintaining its functional presence in plants until the plant organ undergoes natural apoptosis.

(3) Through nano leaf vein absorption technology, special adjustable functions can be achieved without modifying or implanting plant genes.

(4) The disclosure complies with EU safety directive specifications, making it safer to use and conducive to international marketing.

(5) Luminous plants can improve the carbon dioxide solidification efficiency of plants, which can be applied to negative carbon and has the potential in increasing food production in the future.

(6) With unitary, multivariate, or high-entropy compounds, semiconducting or optoelectronic materials that can be designed for energy gap engineering, luminescence spectrum can be effectively adjusted, ornamental value can be improved and plant carbon sequestration and physiological growth functions can be controlled, which will be conducive to applications in net-zero carbon emissions and have the potential in increasing food production in the future.

In order to enable the examiner to have a further understanding and recognition of the technical features of the disclosure, preferred embodiments in conjunction with detailed explanation are provided as follows.

DETAILED DESCRIPTION OF THE DISCLOSURE

Figure 1:
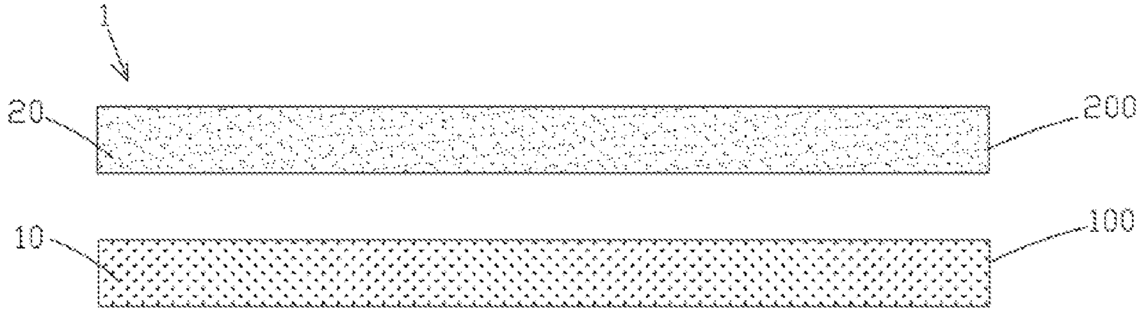
FIG. 1 is a schematic diagram of a leaf vein absorption method and a functional modification material for plant of the disclosure, in which a protector has not yet been covered on a covering.

In order to understand the technical features, content and advantages of the disclosure and its achievable efficacies, the disclosure is described below in detail in conjunction with the figures, and in the form of embodiments, the figures used herein are only for a purpose of schematically supplementing the specification, and may not be true proportions and precise configurations after implementation of the disclosure; and therefore, relationship between the proportions and configurations of the attached figures should not be interpreted to limit the scope of the claims of the disclosure in actual implementation. In addition, in order to facilitate understanding, the same elements in the following embodiments are indicated by the same referenced numbers. And the size and proportions of the components shown in the drawings are for the purpose of explaining the components and their structures only and are not intending to be limiting.

Unless otherwise noted, all terms used in the whole descriptions and claims shall have their common meaning in the related field in the descriptions disclosed herein and in other special descriptions. Some terms used to describe in the present disclosure will be defined below or in other parts of the descriptions as an extra guidance for those skilled in the art to understand the descriptions of the present disclosure.

Moreover, the terms “comprising”, “including”, “having”, and “with” used in the descriptions are all open terms and have the meaning of “comprising but not limited to”.

Figure 2:
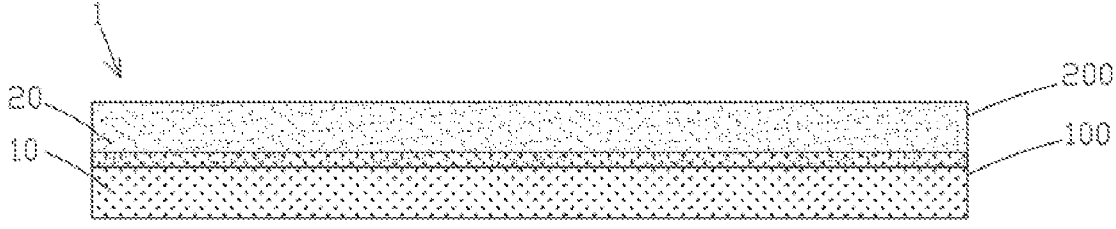
FIG. 2 is a schematic diagram of the leaf vein absorption method and the functional modification material for plant of the disclosure, in which the protector has been covered on the covering.
Figure 3:
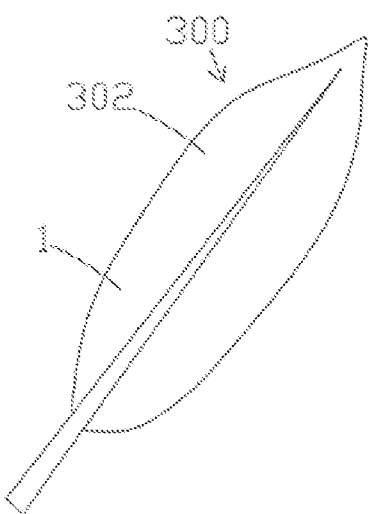
FIG. 3 is a schematic diagram of the leaf vein absorption method and the functional modification material for plant of the disclosure applied to a surface of a plant organ of a plant, in which the plant organ is a leaf or a modified leaf.

Please refer to FIGS. 1 to 3. FIGS. 1 and 2 are schematic diagrams of a functional modification material for plant of the disclosure. FIG. 3 is a schematic diagram of the functional modification material for plant of the disclosure applied to a surface of a plant organ of a plant. Wherein a plant organ 300 shown in FIG. 3 is a leaf. A functional modification material 1 for plant of the disclosure comprises a covering 100 with a functional material 10 and a protector 200 with a polymeric stabilizing material 20. The functional material 10 can be, for example, a unitary, a multivariate, or a high-entropy compound, or a semiconducting or an optoelectronic material. Taking high-entropy material as an example, components of the functional material 10 of the disclosure are, for example, high-entropy oxides or high-entropy oxides-doped semiconductors, wherein high-entropy means containing at least 5 elements with an atomic percentage of 5 to 35. The above are only examples and are not intended to limit the functional material 10 of the disclosure. With semiconducting or optoelectronic materials that can be designed for energy gap engineering, an emission spectrum of unitary, multivariate, or high-entropy compound can be effectively adjusted. For example, if the functional material 10 used in the disclosure is a rare earth element, blue light emission can be produced, if the functional material 10 is a transition element, blue light, green light and red light, or a composite emission can be produced. The disclosure is capable of adjusting a color temperature of the emission spectrum through a proportion of blue light, green light, and red light. The plant organ 300 is, for example, a leaf or a modified leaf, especially a leaf vein. Wherein the plant organ 300 can optionally undergo a pre-treatment step. For example, the disclosure can optionally evenly mix 6.5 g to 16.5 g hydrogen peroxide (HP), 2 g to 30 g polyvinylpyrrolidone (PVP), 3 g to 9 g polyvinyl alcohol (PVA), 1,000 unit/mL to 900,000 unit/mL Nystatin and 550 μL sulfuric acid ($H_2SO_4$, 96%) with 50 g to 500 g deionized water for pretreating an exterior of a surface of the plant organ 300. A plant surface modifier 1 (the functional modification material 1 for plant), the covering 100 and the protector 200 of the disclosure are not limited to various structural forms, forms can be liquid, colloidal, or layered, as long as the plant organ 300 can be covered, any forms are suitable for use in the disclosure. FIGS. 1 and 2 take the layered covering 100 and the layered protector 200 as examples. In the case of the form of a layered structure, it can be optionally maintained in layered form or crushed into crumbs or powder in order to cover the plant organ 300. In addition, the covering 100 and the protector 200 are preferably transparent or translucent. If the covering 100 and the protector 200 are translucent, it is preferable to maintain an original color of the plant organ 300. Dimensions of the covering 100 and the protector 200, such as length, width and thickness, or quantity are not particularly limited, as long as the plant organ 300 can be covered, any dimensions are applicable to the disclosure. Moreover, properties such as density, hardness, and flexibility of the covering 100 and the protector 200 are not particularly limited, as long as the plant organ 300 can be covered, any properties are applicable to the disclosure.

In the disclosure, the covering 100 can be covered on a surface 302 of the plant organ 300 by, for example, spraying, smearing, or coating. Wherein the covering 100 further comprises a stomata expansion material, such as fusicoccin. A content of fusicoccin in the covering 100 is approximately less than or equal to 170 μM. Fusicoccin is capable of promoting expansion of stomata on the surface 302 of the plant organ 300, enabling the stomata to be opened smoothly, which helps the functional material 10 to be absorbed into the plant through the plant organ 300, such as the stomata around veins on leaves. The covering 100 is a water-based material with an adjustable surface charge that has an adhesiveness of a biogel or a biodegradable gel. Wherein the water-based material referred to in the disclosure is, for example, a water-based solvent, and can be, for example, a water-based liquid or aerosol. The biogel is, for example, soft deer gel, hard deer gel, isinglass, cow gel, rabbit gel, granular gel and/or a sanzenbon glue. The biodegradable gel is, for example, polyamide, polyvinylpyrrolidone and/or polyvinyl acetate. A weight percentage of the biogel or the biodegradable gel in the covering 100 is preferably approximately less than or equal to 35%. The biogel or the biodegradable gel adopted in disclosure is capable of degrading by itself. After the functional material 10 is absorbed into the plant, the biogel or the biodegradable gel covering the surface 302 of the plant organ 300 can be decomposed or degraded to avoid hindering growth functions of the plant and damaging the plant. Wherein the water-based material of the covering 100 is, for example, an acidic water-based substance or an alkaline water-based substance, wherein the acidic water-based substance is a water-based solvent containing citric acid, succinic acid, tannic acid, salicylic acid, malic acid, ascorbic acid, gallic acid, hydrochloric acid, nitric acid and/or acetic acid; the alkaline water-based substance is a water-based solvent containing sodium bicarbonate, sodium carbonate, sodium hydroxide, potassium bicarbonate, potassium carbonate and/or potassium hydroxide. Thereby, the covering 100 of the disclosure is a water-based material with an adjustable surface charge that has an adhesiveness of the biogel or the biodegradable gel.

The functional material 10 of the disclosure is not limited to a specific functional material, the functional material 10 can be any material with various functions, in order to perform various functions, for example, any material capable of making the plant irradiate or making the plant to be provided with more properties without poisoning the plant can be applied to be used as the functional material 10. For example, if the functional material 10 is needle-shaped or sea urchin-shaped gold nanoparticles, the functional material 10 can be used as an excitation light source, and the plant can emit light after being irradiated with ultraviolet rays. A particle size of the functional material 10 of the disclosure is much smaller than a pore diameter of the stomata of the plant organ 300 (such as leaf). The functional material 10 is a nanoscale material, a sub-nanoscale material or a micro-nanoscale material. A particle size of the functional material 10 is, for example, 2 μm to 5 nm. A zeta potential formed by a surface charge of the functional material 10 is +0 meV to +75 meV. The zeta potential formed by the surface charge will affect a depth of the functional material 10 entering the plant organ 300. A surface of the functional material 10 with a zeta potential of +5 to +75 meV will help the functional material 10 to enter the palisade cells and even into the chloroplast of the plant. If a zeta potential of the surface of the functional material 10 is −1 to −65 meV, it will help the functional material 10 stay on the plant epidermis to protect the cells. In contrast, plant coating materials in the prior art are mostly only protective agents covering surfaces of plants.

In the disclosure, the protector 200 can be covered on a surface of the covering 100 by, for example, spraying, smearing, or coating, wherein the protector 200 has the polymeric stabilizing material 20 used to stabilize and polymerize the biogel or the biodegradable gel of the protector 200 and/or the covering 100 in order to increase a quantity and a density of the functional material 10 absorbed by the plant organ 300. The polymeric stabilizing material 20 of the protector 200 is, for example, alum ions that stabilize the biogel or the biodegradable gel by polymerization. A weight percentage of the polymeric stabilizing material 20 in the protector 200 is preferably approximately less than or equal to 35%. Wherein the protector 200 is another water-based material with the biogel or the biodegradable gel, wherein a weight percentage of the biogel or the biodegradable gel in the protector 200 is preferably approximately less than or equal to 63%. Wherein the biogel is a soft deer gel, a hard deer gel, an isinglass, a cow gel, a rabbit gel, a granular gel, and/or a sanzenbon glue, and the biodegradable gel is polyamide, polyvinylpyrrolidone and/or polyvinyl acetate.

Wherein another water-based substance of the protector 200 is, for example, an acidic water-based substance or an alkaline water-based substance, wherein the acidic water-based substance is a water-based solvent containing citric acid, succinic acid, tannic acid, salicylic acid, malic acid, ascorbic acid, gallic acid, hydrochloric acid, nitric acid and/or acetic acid; the alkaline water-based substance is a water-based solvent containing sodium bicarbonate, sodium carbonate, sodium hydroxide, potassium bicarbonate, potassium carbonate and/or potassium hydroxide. The protector 200 is sprayed or coated on the surface 302 of the plant organ 300 where the covering 100 has been applied, and the functional material 10 on the surface 302 of the plant organ 300 is covered with the stabilized and polymerized gel to form a protective layer, thereby increasing a quantity and a density of the functional material 10 entering the stomata or leaf veins.

In one embodied mode, taking the covering 100 and the protector 200 in a liquid or colloidal form or even a layered form as an example, a manufacturing method for the covering 100 and the protector 200 of the plant surface modifier 1 (the functional modification material 1 for plant) of the disclosure is as follows. Taking manufacturing of the covering 100 as an example, firstly, mixing a functional material suspension solvent containing the functional material 10 into a water-based solvent using the biogel or the biodegradable gel, thereby forming an adhesive functional material suspension solvent. Wherein the functional material suspension solvent containing the functional material 10 further comprises a stomata expansion material, such as fusicoccin less than or equal to 0 to 170 μM, used to promote expansion of the stomata on the surface 302 of the plant organ 300; and then, mixing the adhesive functional material suspension solvent into an acidic or alkaline water-based solvent to form an adhesive functional material suspension with an adjustable surface charge, which is the functional material suspension solvent to be applied to the plant organ 300 so that the plant organ 300 is covered with the covering 100 of the functional material 10. Taking manufacturing of the protector 200 as an example, mixing the polymeric stabilizing material 20, such as alum ions into a water-based solvent using the biogel or the biodegradable gel to form the protector 200, which can be used to cover the surface of the covering 100 as described above. An ion concentration in the solvent is 0-20% by weight. The ions are capable of stabilizing the biogel or the biodegradable gel by polymerization.

Carbon sequestration tests are conducted with common indoor plant dieffenbachia (average 235 g). After a 15-day cycle light test (1/10 daylight for 8 hours a day), general dieffenbachia and luminous dieffenbachia can sequester 856 mg of carbon. 50% of leaf surface of luminous dieffenbachia applied with leaf vein absorption can sequester 1204 mg of carbon, increasing the carbon sequestration capabilities by 40.6%. Luminous plants can create a new experience of plant viewing at night, and carbon capture and carbon neutrality can be achieved at the same time, increasing the carbon sequestration capabilities by 40.6%.

In summary, in the leaf vein absorption method and the functional modification material for plant of the disclosure, with the brand-new plant surface functional modification technology, through the modification technology the plant surface is capable of effectively producing special physical or chemical functions, and after modification, the plant can still grow naturally, and therefore the disclosure can be widely applied to natural plants to be capable of effectively advancing progress in horticultural and agricultural functional plants. In addition, using the plant surface modification technology, the plant surface functions still exist and can coexist. The functional material is capable of maintaining its functions on the plant surface until the plant organ undergoes natural apoptosis. Through the plant surface modification technology, special functions can be achieved without modifying or implanting plant genes.

Note that the specification relating to the above embodiments should be construed as exemplary rather than as limitative of the present disclosure, with many variations and modifications being readily attainable by a person of average skill in the art without departing from the spirit or scope thereof as defined by the appended claims and their legal equivalents.

What is claimed is:

1. A leaf vein absorption method comprising following steps of:

performing a pre-treatment step on an exterior of a surface of a plant organ of a plant by applying thereto a mixture of 6.5 g to 16.5 g hydrogen peroxide (HP), 2 g to 30 g polyvinylpyrrolidone (PVP), 3 g to 9 g polyvinyl alcohol (PVA), 1,000 Unit/mL to 900,000 Unit/mL nystatin, and 550 μL sulfuric acid ($H_2SO_4$, 96%) mixed with 50 g to 500 g deionized water;

mixing a functional material suspension solvent containing a functional material into a water-based solvent comprising a biogel or a biodegradable gel, thereby forming an adhesive functional material suspension solvent, wherein the functional material is configured to cause the plant to emit light with an adjustable color temperature of an emission spectrum;

mixing the adhesive functional material suspension solvent into an acidic or alkaline water-based solvent, thereby forming an adhesive functional material suspension with an adjustable surface charge to serve as a covering with a functional material;

covering the surface of the plant organ of the plant with the covering, wherein the functional material suspension solvent containing the functional material further comprises a stomata expansion material for promoting expansion of a plurality of stomata on the surface of the plant organ to enable the functional material to be absorbed into the plant through a plurality of leaf veins of the plant organ, wherein a content of the stomata expansion material in the covering is 170 μM, a zeta potential formed by a surface charge of the functional material is +75 meV, and the plant organ is a leaf or a modified leaf;

mixing a polymeric stabilizing material into another water-based solvent comprising a biogel or a biodegradable gel, thereby forming a protector, wherein a weight percentage of the polymeric stabilizing material in the protector is 35%, and a weight percentage of the biogel or the biodegradable gel in the protector is 63%; and covering a surface of the covering with the protector, wherein the polymeric stabilizing material is used to stabilize and polymerize the biogel or the biodegradable gel of the protector and/or the covering, thereby increasing a quantity and a density of the functional material absorbed by the plant organ, and capable of increasing carbon sequestration capacity of the plant.

2. The leaf vein absorption method as claimed in claim 1, wherein the biogel of the protector and/or the covering is a granular gel, and the biodegradable gel is polyamide, polyvinylpyrrolidone and/or polyvinyl acetate.

3. The leaf vein absorption method as claimed in claim 1, wherein the stomata expansion material is fusicoccin, and the polymeric stabilizing material is potassium aluminum sulfate.

4. The leaf vein absorption method as claimed in claim 1, wherein the covering is covered on the plant organ by spraying, smearing, or coating, and the protector is covered on the covering by spraying, smearing, or coating.

5. The leaf vein absorption method as claimed in claim 1, wherein a particle size of the functional material is 2 μm to 5 nm.

6. The leaf vein absorption method as claimed in claim 1, wherein the plant is an indoor plant, and when the plant is Dieffenbachia, the carbon sequestration capacity of the plant increases by 40.6% through a light test with a 15-day cycle and 1/10 solar irradiation out of 8 hours a day.

* * * * *